United States Patent [19]

Mandal et al.

[11] Patent Number: 5,145,994
[45] Date of Patent: Sep. 8, 1992

[54] 4-HYDROXYPHENYL ACETIC ACID

[75] Inventors: Arun K. Mandal, Thane; Satish W. Mahajan, New Bombay; Damodar G. Jawalkar, Taluka Haveli, all of India

[73] Assignee: ICI India Limited, West Bengal, India

[21] Appl. No.: 737,042

[22] Filed: Jul. 29, 1991

[51] Int. Cl.$^5$ .............................................. C07C 65/01
[52] U.S. Cl. ................................................... 562/478
[58] Field of Search ......................................... 562/478

[56]  References Cited

FOREIGN PATENT DOCUMENTS 2445311  8/1980  France .
5092344  12/1980  Japan .

OTHER PUBLICATIONS

CA 104(3):19415b 1985.

*Primary Examiner*—Paul J. Killos
*Attorney, Agent, or Firm*—Ladas & Parry

[57]  ABSTRACT

A process for the preparation of 4-hydroxyphenyl acetic acid of the formula I, an important raw material for the preparation of pharmaceutically active substances, from sodium-4-hydroxymandalate monohydrate comprising reducing the sodium-4-hydroxymandalate monohydrate with a reducing agent consisting of stoichiometric quantity of a phosphorus (III) compound and catalytic or stoichiometric quantity of sulphur dioxide or equivalent salt thereof in a solvent at 60°–120° C. and at ambient to 5 atmospheres pressures.

2 Claims, No Drawings

4-HYDROXYPHENYL ACETIC ACID

This invention relates to 4-hydroxyphenyl acetic acid of the formula I shown in the accompanying drawings and a process for the manufacture thereof from sodium-4-hydroxymandalate monohydrate of the formula III shown in the accompanying drawings.

4-Hydroxyphenyl acetic acid of the formula I is an important raw material for the preparation of pharmaceutically active substances. For example, 4-hydroxyphenyl acetic acid of the formula I can be conveniently converted into 4-hydroxyphenyl acetamide of the formula II shown in the accompanying drawings which is an important intermediate for the manufacture of atenolol, an active cardiovascular drug.

Some of the processes known in the prior art for the manufacture of 4-hydroxyphenyl acetic acid of the formula I are the following:

i) Reduction of sodium-4-hydroxymandalate monohydrate (SHM) of the formula III with stannous chloride in mineral acids (British Patent No.2,078,718).

ii) Reduction of SHM of the formula III with zinc and catalytic quantity of chromium (III) chloride in sulphuric acid (Belgian Patent No.867,289).

iii) Reduction of SHM of the formula III with phosphorus acid catalysed by 57% hydrogen iodide (French Patent No.2588869).

iv) Hydrogenolysis of SHM of the formula III with hydrogen catalysed by palladium on carbon (British Patent no.207811 and Japanese Patent no. 5,852,242).

Tin, zinc and chromium being toxic to environment and human beings, their use in the above conventional processes (i) and (ii) creates pollution. Hydrogen iodide liquid used in the above conventional process (iii) is costly. Palladium used in the above conventional process (iv) is also very expensive.

An object of the present invention is to obviate the above drawbacks and provide an economic and simple and convenient and easy to carry out process for the preparation of 4-hydroxyphenyl acetic acid of the formula I from sodium-4-hydroxymandalate monohydrate of the formula III.

Another object of the present invention is to provide 4-hydroxyphenyl acetic acid of the formula I obtained by the process thereof.

According to the present invention there is provided a process for the preparation of 4-hydroxyphenyl acetic acid of the formula I from sodium-4-hydroxymandalate monohydrate of the formula III comprising reducing sodium-4-hydroxymandalate monohydrate of the formula III with a reducing agent consisting of stoichiometric quantity of a phosphorus (III) compound and catalytic or stoichiometric quantity of sulphur dioxide or equivalent salt thereof in the presence of a solvent at 60°–120° C. and at ambient to 5 atmospheres pressures.

The solvent used in the process of the present invention is, for example, water, acetic acid, water-acetic acid mixture or water-hydrochloric mixture, preferably water.

The phosphorus (III) compound used in the process of the present invention is, for example, phosphorus acid or phosphorus acid ester such as trialkyl phosphite such as triethylphosphite, preferably phosphorus acid.

The preferred reaction temperature is 100° C.

The equivalent salt of sulphur dioxide is, for example, alkali metal bisulphite or sulphite such as sodium bisulphite or sodium sulphite or alkaline earth metal bisulphite or sulphite such as calcium bisulphite or sulphite, the alkali metal bisulphite or sulphite being the preferred one.

The reduction reaction of the present invention can be accelerated by carrying it out at above ambient pressure up to 5 atmospheres.

The compound of the formula I is isolated from the reaction mixture in known manner, for instance, by cooling the reaction mixture to ambient temperature, filtering out the crystals and drying the crystals to a constant weight; alternatively the compound of the formula I is isolated from the reduction reaction mixture by cooling the reaction mixture to ambient temperature, extracting the reaction mixture with an organic solvent such as ethyl acetate, diethyl ether or methyl isobutyl ketone, drying the organic layer over anhydrous sodium sulphate and removing the organic solvent from the organic layer by distillation.

The starting material SHM of the formula III can be obtained by the condensation of phenol and glyoxylic acid (British Patent No. 1576331).

The following examples are illustrative of the present invention but not limitative of the scope thereof. The identity and purity of the product in the examples were confirmed by spectroscopic and High Pressure Liquid Chromatography (HPLC) analysis.

EXAMPLE 1

A mixture of sodium-4-hydroxymandalate monohydrate (104 g, 90% w/w, 0.45 mole) phosphorus acid (41 g, 0.5 mole) and sodium bisulphite (52 g, 0.5 mole) in water 415 ml) was heated at 100° C. for 4 hours at a pressure of 20 p.s.i. (pounds per square inch). The reaction mixture was cooled to ambient temperature (25° C.) and the crystallised product (4-hydroxyphenyl acetic acid) was filtered out and dried to a constant weight.

| | |
|---|---|
| Yield | 58 gm, 85% |
| MP | 147–149° C. |
| Purity | 99% |

EXAMPLE 2

The procedure of example 1 was repeated except for the difference that the reaction was carried out for 12 hours at ambient pressure.

| | |
|---|---|
| Yield | 51.3 gm, 75% |
| MP | 147–149° C. |
| Purity | 99% |

EXAMPLE 3

The procedure of example 1 was repeated except for the difference that the reaction mixture after cooling was extracted with ethyl acetate (3×120 ml), the organic layer was dried over anhydrous sodium sulphate and the ethyl acetate was removed from the organic layer by distillation.

| | |
|---|---|
| Yield | 62 g, 90% |
| MP | 147–150° C. |
| Purity | 96% |

EXAMPLE 4

The procedure of example 1 was repeated except for the difference that 0.33 moles of sodium bisulphite were used. The reaction mixture was worked up as described in example 3.

| Yield | 62.2 g, 91% |
|---|---|
| MP | 147–150° C. |
| Purity | 96.2% |

EXAMPLE 5

The procedure of example 1 was repeated except for the difference that triethyl phosphite (83 g, 0.5 mole) was used instead of phosphorus acid.

| Yield | 57.9 g, 85% |
|---|---|
| MP | 146–149° C. |
| Purity | 96% |

EXAMPLE 6

The procedure of example 1 was repeated except for the difference that 310 ml water was used.

| Yield | 61.5 g, 90% |
|---|---|
| MP | 147–150° C. |
| Purity | 95% |

EXAMPLE 7

The procedure of example 1 was repeated except for the difference that 350 ml water was used. The reaction mixture was worked up as described in example 3.

| Yield | 61.00 g, 89% |
|---|---|
| MP | 147–150° C. |
| Purity | 96% |

EXAMPLE 8

The procedure of example 1 was repeated except for the difference that 0.65 moles of sodium bisulphite were used.

| Yield | 62.00 g, 90% |
|---|---|
| MP | 147–150° C. |
| Purity | 96% |

EXAMPLE 9

The procedure of example 1 was repeated except for the difference that 0.25 moles of sodium bisulphite were used. The reaction mixture was worked up as described in example 3.

| Yield | 62.5 g, 91% |
|---|---|
| MP | 147–150° C. |
| Purity | 94% |

EXAMPLE 10

The procedure of example 1 was repeated except for the difference that 0.16 moles of sodium bisulphite were used.

| Yield | 63 g, 92% |
|---|---|
| MP | 147–150 C. |
| Purity | 95% |

EXAMPLE 11

The procedure of example 1 was repeated except for the difference that 0.5 moles of sodium bisulphite were used.

| Yield | 51 g, 75% |
|---|---|
| MP | 147–150° C. |
| Purity | 94% |

EXAMPLE 12

The procedure of example 1 was repeated except for the difference that 1.0 mole of sodium bisulphite were used. The reaction mixture was worked up as described in example 3.

| Yield | 53.3 g, 78% |
|---|---|
| MP | 147–150° C. |
| Purity | 94% |

The process of the present invention does not create pollution and is, therefore, advantageous over the conventional processes i and ii in that it does not use toxic tin, zinc and chromium. The process of the present invention is economical and, therefore, advantageous over the conventional process iii in that it does not use hydrogen iodide and instead uses sulphur dioxide or its equivalent salt which is cheaper to hydrogen iodide. The process of the present invention is economical and, therefore, advantageous over the conventional process iv in that it does not use expensive palladium. The isolation of the product as per the process of the present invention is very simple, easy and convenient as can be seen in the examples. Therefore, the process of the present invention is simple, convenient and easy to carry out. Use of water as the solvent also makes the process of the present invention simple, easy and convenient to carry out, besides economical.

We claim:

1. A process for the preparation of 4-hydroxyphenyl acetic acid of the formula:

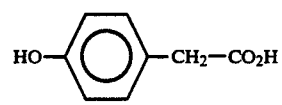

from sodium-4-hydroxy-mandalate monohydrate of the formula:

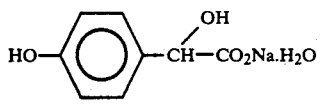

comprising reducing the sodium-4-hydroxy-mandalate monohydrate with a reducing agent consisting of stoichiometric quantity of a phosphorus (III) compound and a catalytic or stoichiometric quantity of sulphur dioxide or equivalent salt thereof in the presence of a solvent at 60°–120° C. and at ambient to 5 atmospheres pressures.

2. A process as claimed in claim 1, wherein the solvent is water and the phosphorus (III) compound is phosphorus acid, and the equivalent salt of sulphur dioxide is alkali metal bisulphite or sulphite and the reduction reaction is carried out at 100° C.

* * * * *